(12) United States Patent
Tani et al.

(10) Patent No.: US 9,289,260 B2
(45) Date of Patent: Mar. 22, 2016

(54) MICROWAVE SURGICAL DEVICE

(75) Inventors: Tohru Tani, Otsu (JP); Shigeyuki Naka, Otsu (JP)

(73) Assignee: NATIONAL UNIVERSITY CORPORATION SHIGA UNIVERSITY OF MEDICAL SCIENCE, Shiga (JP)

( * ) Notice: Subject to any disclaimer, the term of this patent is extended or adjusted under 35 U.S.C. 154(b) by 595 days.

(21) Appl. No.: 12/531,299

(22) PCT Filed: Mar. 25, 2008

(86) PCT No.: PCT/JP2008/055515
§ 371 (c)(1),
(2), (4) Date: Sep. 14, 2009

(87) PCT Pub. No.: WO2008/117789
PCT Pub. Date: Oct. 2, 2008

(65) Prior Publication Data
US 2010/0042090 A1    Feb. 18, 2010

(30) Foreign Application Priority Data

Mar. 27, 2007  (JP) ................................. 2007-083136

(51) Int. Cl.
*A61B 18/18*    (2006.01)
*A61B 18/00*    (2006.01)
(52) U.S. Cl.
CPC ............. *A61B 18/18* (2013.01); *A61B 18/1815* (2013.01); *A61B 2018/00702* (2013.01); *A61B 2018/00875* (2013.01)
(58) Field of Classification Search
CPC ........ A61B 18/08; A61B 18/10; A61B 18/12; A61B 18/1206; A61B 18/18; A61B 18/1815; A61B 2018/126; A61B 2018/00607; A61B 2018/0063; A61B 2018/00642; A61B 2018/00702; A61B 2018/00595; A61B 2018/00589; A61B 2018/0016; A61B 2018/1226; A61B 2018/1266; A61B 2018/00958; A61B 17/28; A61B 17/29
USPC ................................................ 606/27–51, 52
See application file for complete search history.

(56) References Cited

U.S. PATENT DOCUMENTS 4,474,179 A    10/1984 Koch
4,494,539 A    1/1985  Zenitani
(Continued)

FOREIGN PATENT DOCUMENTS

JP    09-117456 A    5/1997
JP    09-117456 A    5/1997
(Continued)

*Primary Examiner* — Michael Peffley
*Assistant Examiner* — Khadijeh Vahdat
(74) *Attorney, Agent, or Firm* — Joseph H. Kim; JHK Law

(57) ABSTRACT

The solution of the problem to be solved is the provision of a means for determining timing both accurately and securely at which a treatment is shifted from gripping and coagulation (hemostasis or sealing) to resection by using a multifunctional treatment tool capable of exfoliation, gripping, coagulation (hemostasis or sealing) and resection of the treated region in a bipolar microwave treatment tool. A microwave surgical device control method and a device, in which the completion of coagulation (hemostasis or sealing) of tissue is detected and a microwave oscillation output is controlled by making use of the change in the direct current electric resistance value due to the reduction in the amount of water as the temperature rise of the tissue at the time of heating and coagulation of the tissue in the treated region with microwaves.

3 Claims, 2 Drawing Sheets

(56) References Cited

U.S. PATENT DOCUMENTS

| | | | |
|---|---|---|---|
| 5,558,671 A * | 9/1996 | Yates | 606/38 |
| 5,707,369 A * | 1/1998 | Vaitekunas et al. | 606/31 |
| 5,836,943 A * | 11/1998 | Miller, III | 606/34 |
| 6,383,183 B1 * | 5/2002 | Sekino et al. | 606/34 |
| 2001/0001819 A1 | 5/2001 | Lee et al. | |
| 2002/0026225 A1 * | 2/2002 | Segal | 607/89 |
| 2003/0050633 A1 * | 3/2003 | Ellman et al. | 606/37 |
| 2003/0158551 A1 * | 8/2003 | Paton et al. | 606/51 |
| 2003/0199863 A1 | 10/2003 | Swanson et al. | |
| 2007/0054539 A1 | 3/2007 | Wakikaido | |
| 2007/0173811 A1 * | 7/2007 | Couture et al. | 606/39 |
| 2009/0018653 A1 * | 1/2009 | Bashiri et al. | 623/11.11 |

FOREIGN PATENT DOCUMENTS

| | | |
|---|---|---|
| JP | 2732675 B2 | 3/1998 |
| JP | 2001-037775 A | 2/2001 |
| JP | 2001-037775 A | 2/2001 |
| WO | WO 97/33524 A1 | 9/1997 |
| WO | WO 2008/117789 A1 | 10/2008 |

* cited by examiner

MICROWAVE SURGICAL DEVICE

TECHNICAL FIELD

The present invention relates to a microwave surgical device control method comprising the step of detecting the completion of coagulation (evaporation and desiccation of the tissue), hemostasis or tissue sealing and controlling a microwave (high-frequency wave) oscillation output when the tissue in a treated region is heated and coagulated with microwaves. Further, the present invention relates to a microwave surgical device that has a function to detect the completion of enough coagulation (hemostasis or sealing) and a function to control a microwave oscillation output and which performs hemostasis, coagulation, sealing, incision, and etc., by coagulating body tissue in the vicinity of the electrode through microwave irradiation from the surgical electrode.

The present application claims priority from Japanese Patent Application Number 2007-083136, the content of which is incorporated herein by reference.

BACKGROUND ART

Conventionally, a microwave surgical device of this type is formed by connecting a mono-polar surgical electrode in the shape of a needle to the main device via a coaxial cable, in such a manner that the surgical electrode can be exchanged with another freely, as described in JP 01-20619 B (A61B 17/39), JP 01-20617 B (A61B 17/36), etc.

When the surgical electrode is inserted into body tissue, a microwave generator of the main device is operated and microwaves (2,450 MHz) are supplied to the surgical electrode. Then, the inside of the body tissue is irradiated with the convergent microwaves from the electrode and the tissue in the vicinity of the electrode is coagulated by the dielectric heat energy that is generated in the organism.

By repeating this, operations on the body tissue, such as hemostasis, coagulation, incision, tissue sealing, and resection, can be performed and in particular, the hemostasis/sealing effect is great, and therefore, the microwave surgical device of this type is very useful for operations on solid internal organs, such as the liver, which are fragile and contain a lot of blood.

When coagulation by each one-time microwave irradiation is completed, normally, a tissue dissociating direct current is supplied from the main device to the surgical electrode, with its main conductor as a negative electrode and an external conductor as a positive electrode, and the tissue that has stuck to the surgical electrode is softened by the electro-osmotic action of the organism based on the current and, as a result, the surgical electrode can be easily separated from the body tissue.

Further, though the surface of the treatment tool of the microwave surgical device of this type is sometimes coated with Teflon (registered trademark), ceramic, and the like, there is a possibility of risk that the coating material may be broken, dislocated, etc. when it is separated.

[Patent document 1] JP 01-20619 B
[Patent document 2] JP 01-20617 B

DISCLOSURE OF THE INVENTION

In a bipolar microwave treatment tool, when a treatment is shifted from gripping and coagulation (hemostasis or sealing) to its resection by using a single treatment tool that is a multifunctional treatment tool capable of exfoliating, gripping, coagulating (hemostasis or sealing) and resection the treated region, there may be a case of bleeding due to uncompleted hemostasis, under an incorrect timing condition. Further, the bipolar treatment tool may short-circuit electrically at the time of resection because both the electrodes come into contact with each other.

One objective of the present invention is to provide a device that enables safe use of a bipolar microwave (high-frequency wave) multifunctional treatment tool by solving these problems.

In the case of a conventional microwave surgical device of this type, it is not possible to detect the alteration of a layer coagulated by microwave irradiation, and therefore, a doctor or a medical technician sets a timer for the output time of microwave based on experience and intuition and each one-time coagulation is completed by the irradiation of microwave to body tissue for the set period of time (about 10 seconds). However, the alteration of the coagulated layer by microwave irradiation differs depending on the shape of the surgical electrode, the conditions of body tissue, or the like, and therefore, it is not easy to complete coagulation at an appropriate timing (minimum and enough) with the conventional device, and there is a problem that the body tissue is carbonated when the surgical electrode causes a small spark discharge due to hypercoagulation, or that the tissue sticks to the electrode.

Another objective of the present invention is to provide a means for automatically completing the coagulation of body tissue by microwave irradiation at an appropriate timing.

The present invention includes:

1. A microwave surgical device control method comprising the step of detecting the completion of coagulation (hemostasis or sealing) of tissue and controlling a microwave (high-frequency wave) oscillation output by making use of the change in the direct current electric resistance value due to the reduction in the amount of water as the temperature rise of the tissue at the time of heating and coagulation of the tissue in a treated region with microwaves; and 2. A microwave surgical device comprising an output timer that controls the output time of microwaves, a microwave generator that produces microwaves, an output control part that controls the output of the said microwave generator, a coaxial cable supplied with microwaves from the said microwave generator, a surgical electrode that is connected to the tip end of the said coaxial cable and inserted into body tissue, and which is capable of gripping the tissue to be coagulated, a battery or constant voltage power supply, a variable resistor combined with a direct current voltage meter relay, a direct current microwave mixer, an oscillator control circuit that connects the direct current voltage meter relay and a microwave oscillator, and a determination processing part that includes a circuit that connects the variable resistor and the direct current microwave mixer, determines the completion timing of said coagulation by the change in the direct current electric resistance value, and notifies said microwave generator of the termination of the microwave output via said oscillator control circuit and said output control part.

According to the present invention, it is possible to detect the completion of coagulation (hemostasis or sealing) of tissue and determine the completion of coagulation at an appropriate timing depending on the conditions etc. of the body tissue by making use of the change in the direct current electric resistance value due to the reduction in the amount of water in the tissue with the advancement of the coagulation of the body tissue by irradiation of microwave.

Then, since the output of microwave is terminated based on this determination, it is possible to automatically complete the coagulation of body tissue by irradiation of microwave at an appropriate timing (minimum and enough), to prevent without fail the occurrence of so-called hypercoagulation and uncompleted coagulation, and to considerably improve its operability and functionality without an excess impairment.

DESCRIPTION OF THE PREFERRED EMBODIMENT

In order to achieve the above-mentioned object, a microwave surgical device of the present invention comprises an output time setting part that sets the output time of microwaves, a microwave generator that outputs microwaves, an output control part that controls the output of said microwave generator, a coaxial cable supplied with microwaves from said microwave generator, a surgical electrode that is connected to the tip end of said coaxial cable and inserted into body tissue, and which is capable of gripping the tissue to be coagulated, a battery or constant voltage power supply, a variable resistor combined with a direct current voltage meter relay, a direct current microwave mixer, an oscillator control circuit that connects the direct current voltage meter relay and a microwave oscillator, and a determination processing part that includes a circuit that connects the variable resistor and the direct current microwave mixer, determines the completion timing of said coagulation by the change in the direct current electric resistance value, and notifies said microwave generator of the termination of the microwave output via said oscillator control circuit and said output control part.

Then, the completion of coagulation (hemostasis or sealing) of tissue is detected and the microwave oscillation output of the microwave surgical device is controlled by making use of the change in the direct current electric resistance value due to the reduction in the amount of water as the temperature of the tissue rises when the tissue in a treated region is heated and coagulated with microwaves.

That is, the determination processing part determines the completion of coagulation at an appropriate timing depending on the conditions etc. of the body tissue by monitoring the direct current electric resistance value.

Then, since the output of microwaves is terminated based on this determination, the coagulation of body tissue by irradiation of microwave is automatically completed at an appropriate timing.

In this system, there are some cases where the operating points of the meter relay may differ depending on the difference in shape and size of the electrode to be used and the difference in surface area of the electrode that comes into contact with the tissue of the treated region. As countermeasures, it is possible to automatically set the operating point of each electrode when a plug attached to the electrode is inserted for each electrode.

Figure 1:
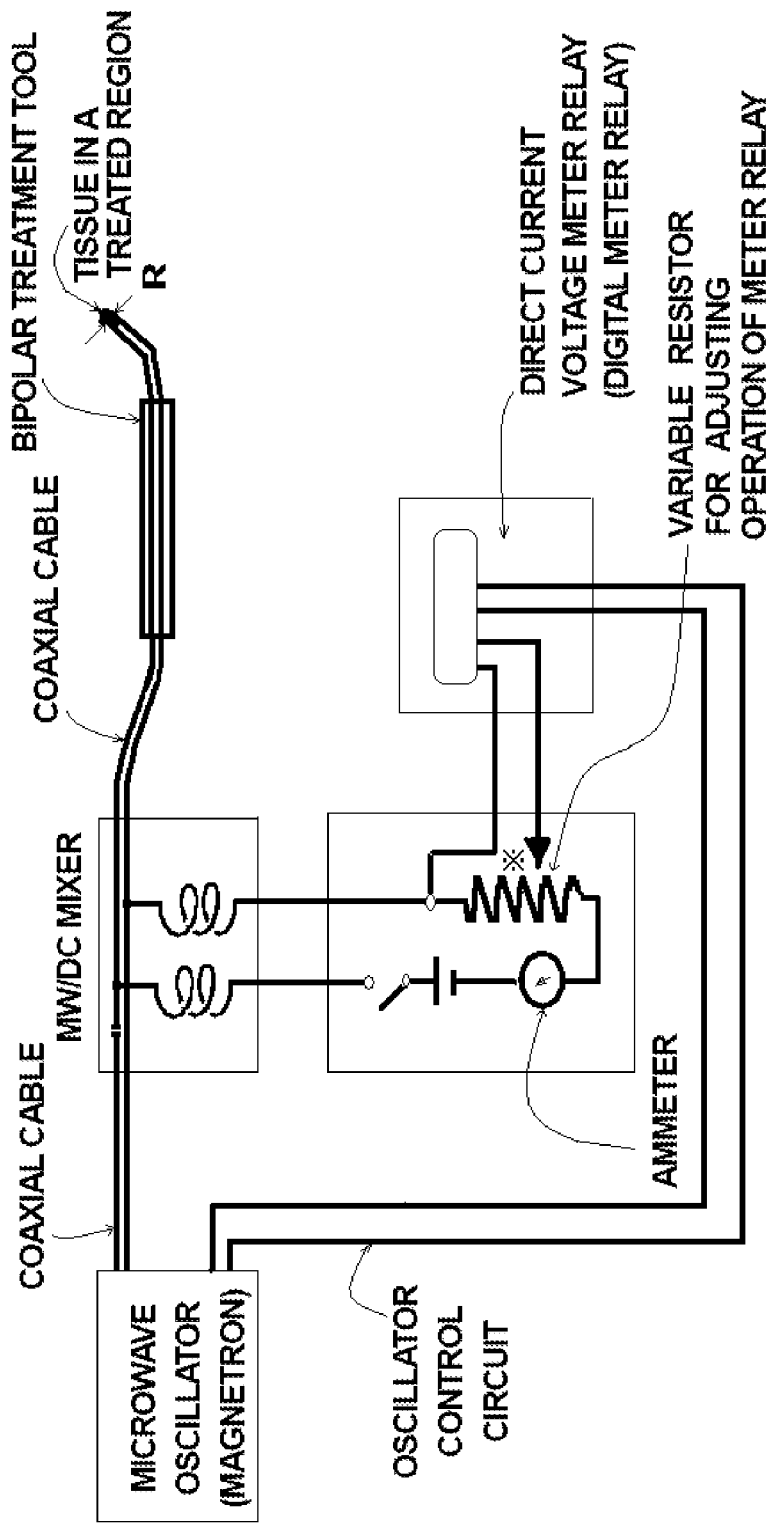
FIG. 1 is an overall view of a device of the present invention.

The timing of resection of the tissue to be treated is detected as shown in FIG. 1. Due to the passage of microwaves being output in an overlapping manner, the tissue of the treated region is heated, water is evaporated and is reduced in amount, and the electric resistance value of the tissue changes, and as a result of which, an amount of direct current that flows through the tissue of the treated region held (gripped) at the tip end of the bipolar treatment tool reduces through the direct current mixer inserted into the microwave output circuit, and therefore, the voltage changes at the * mark of the variable resistor (VR) that combines the battery or constant voltage power supply and the direct current voltage meter relay. Depending on this change, the direct current voltage meter relay operates to emit a signal indicative of the completion of coagulation and at the same time, the output of the microwave oscillator is controlled via the microwave oscillator control circuit. In this connection, it is possible to arbitrarily set the value at which the meter relay operates by adjusting the * mark (of the VR). When both electrodes come into contact with each other (short circuit) at the time of the resection of the tissue of the treated region with the bipolar treatment tool, the electric resistance value at the R part in the figure comes to zero. Therefore, the voltage at the * mark (of the VR) changes and it is possible to terminate the oscillation of microwave instantaneously, and therefore, it is possible to continue the resection of the tissue to be treated. This system can be used for any application such as under the direct visual sight, through the mirrored view, through an endoscope, or through a catheter.

An embodiment of the present invention will be explained with reference to FIG. 1. FIG. 1 shows an overall configuration, in which a coaxial cable is connected to a microwave oscillator by a connector in such a manner that the coaxial cable can be connected and disconnected to the tip end of the coaxial cable, a bipolar surgical electrode is replaceably connected by a connector. Then, it is possible for the surgical electrode to grip body tissue at its tip end. To the coaxial cable, a direct current is connected from a battery or constant voltage power supply through a microwave/direct current mixer and then is connected to a variable resistor for adjusting the operation of a meter relay, a direct current voltage meter relay, and a microwave oscillator control circuit.

Figure 2:
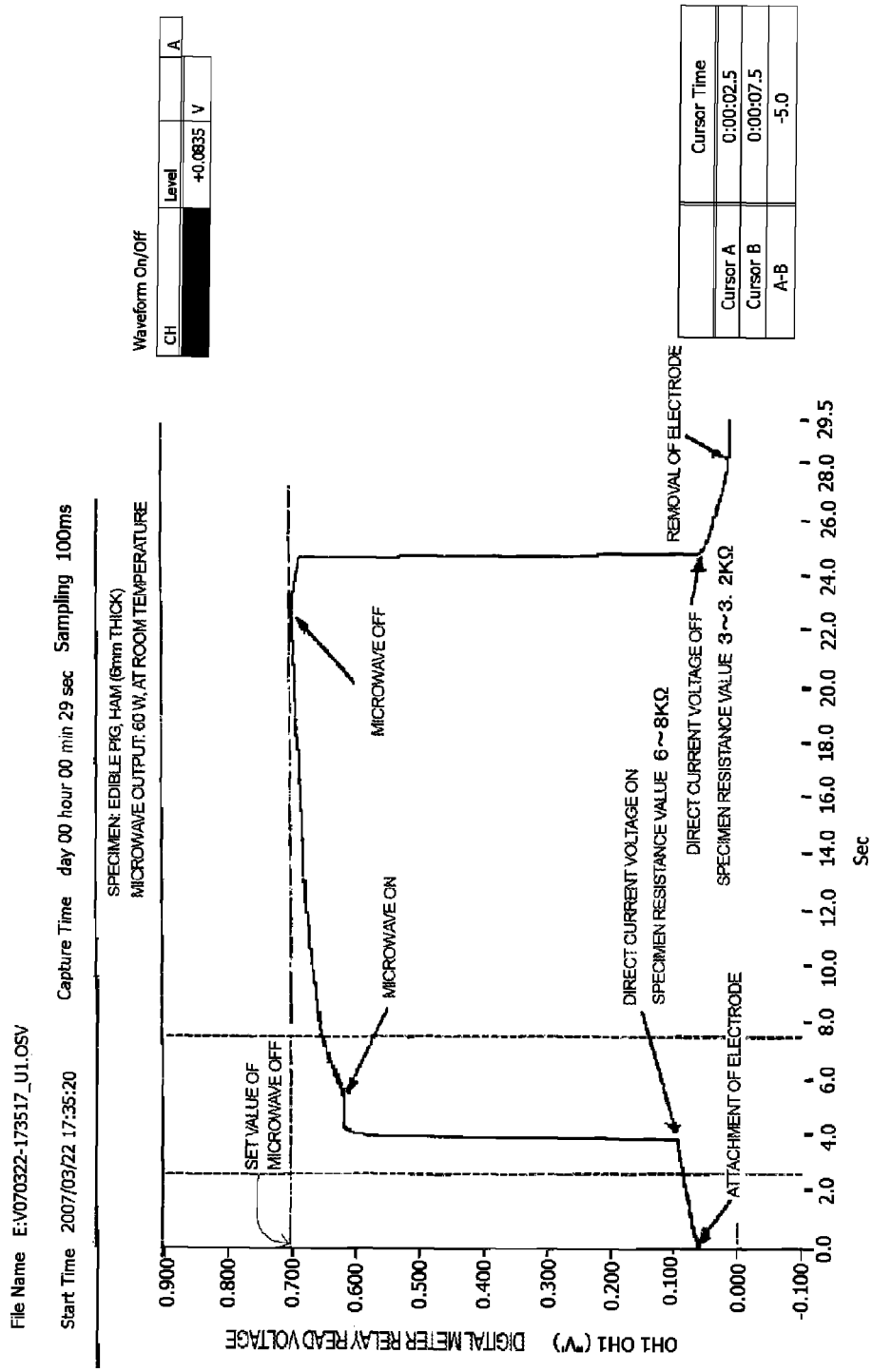
FIG. 2 shows the turning-on/off of microwaves by the device of the present invention.

FIG. 2 shows the turning on/off of microwaves in accordance with the device of the present invention. The experiment uses a ham (6 mm thick) of an edible pig and is conducted while the ham is gripped at the tip end of the surgical electrode at room temperature by using microwaves of 2,450 MHz (60 W). In a state where microwaves are not applied, the resistance value of the specimen is 6 to 8 KΩ. The direct current voltage is turned on (at first, 0.1 V), the microwave is turned on at about 0.6 V, then the specimen is irradiated with microwaves for about 20 seconds, and when the voltage reads about 0.7 V, it is determined that the coagulation of tissue is completed, and the microwave is turned off. Then, at a voltage of about 0.8 V, the direct current voltage is also turned off.

In addition, in the present invention, microwaves of 900 to 6,000 MHz can be made use of in an equivalent manner.

INDUSTRIAL APPLICABILITY

The treatment tool of the present invention can be expected to be very useful in the medical field because the coagulation by irradiation of microwave is completed at an appropriate completion timing, the occurrence of the hypercoagulation or the uncompleted coagulation can be prevented without fail, the uniform processing without depending on experience of an operator becomes possible, and its operability and functionality are improved remarkably.

The invention claimed is:

1. A method for controlling a microwave surgical device having an oscillator, a coaxial cable supplied with a microwave energy from said oscillator, a first surgical electrode and a second surgical electrode pivotally connected that are connected to said coaxial cable to apply a microwave energy to tissue, a battery or constant voltage power supply, and a microwave/direct current mixer connected to said coaxial cable comprising:

contacting a tissue to be coagulated by the first surgical electrode and the second surgical electrode;

irradiating the tissue with microwave energy by the first surgical electrode and the second surgical electrode;

supplying a direct current voltage to the tissue so as to provide a direct current electric resistance value in the tissue by the first surgical electrode and the second surgical electrode; and detecting completion of the coagulation of the tissue by detecting a change in the direct current electric resistance value in the tissue due to reduction in an amount of water in the tissue as temperature in the tissue rises from irradiating the tissue with the microwave energy, and wherein the direct current voltage is supplied from the battery or constant voltage power supply through the microwave/direct current mixer, and the microwave energy is supplied from the oscillator.

2. The method according to claim 1, wherein the coagulation results in hemostasis.

3. The method according to claim 1, wherein the coagulation results in sealing of tissue.

* * * * *